United States Patent [19]

Zimmerman et al.

[11] 4,001,248
[45] Jan. 4, 1977

[54] N-CYCLOALKYLMETHYL DECAHYDROISOQUINOLINES

[75] Inventors: Dennis M. Zimmerman, Indianapolis; Winston S. Marshall, Bargersville, both of Ind.

[73] Assignee: Eli Lilly and Company, Indianapolis, Ind.

[22] Filed: June 7, 1974

[21] Appl. No.: 477,222

[52] U.S. Cl. .................. 260/289 D; 260/286 Q; 260/286 R; 260/287 D; 260/289 C; 260/326.1; 260/326.16; 260/258.1
[51] Int. Cl.² ...................................... C07D 217/04
[58] Field of Search .................. 260/289 D, 287 D

[56] References Cited

FOREIGN PATENTS OR APPLICATIONS 802,557   7/1973   Belgium .............................. 260/289

*Primary Examiner*—R. Gallagher
*Assistant Examiner*—Mary C. Vaughn
*Attorney, Agent, or Firm*—James L. Rowe; Everet F. Smith

[57] ABSTRACT

1-Cycloalkylmethyl-3a-(substituted-phenyl) decahydroisoquinolines, useful as analgetic agonists or analgetic antagonists.

9 Claims, No Drawings

N-CYCLOALKYLMETHYL DECAHYDROISOQUINOLINES

BACKGROUND OF THE INVENTION

It has long been known that slight chemical modifications of the morphine molecule lead to analgesic agonists of widely differing potency and addictive properties. For example, codeine, the methyl ether of morphine, is a relatively mild analgesic agonist having slight dependance (addiction) liability. On the other hand, heroin, the diacetyl derivative of morphine, is a powerful agonist with extremely high addiction potential. In addition, as long as 1915, Pohl found that when the N-methyl group of codeine was replace with an allyl group, the resulting compound, N-allylnorcodeine, was an opiate antagonist. In 1940, N-allylnormorphine or nalorphine was synthesized and was shown to have a highly specific ability to reverse the depressant effects of morphine. Other simple chemical modifications of the morphine molecule have yielded many interesting drugs. Thus, one fruitful research area in the search for improved analgesics of high potency and/or lower dependance (addiction) liability has been the chemical modification of the morphine molecule.

In addition to modifying the morphine ring structure by chemical means, chemists have developed a second related field of research—the preparation of certain morphine partstructures—with the same end in mind as above; i.e., the synthesis of improved analgesic agonists and/or analgesic antagonists of improved properties. For example, meperidine, a widely used analgesic, can be written as a morphine part-structure. Many other morphine part-structures have been prepared, some of which have improved analgesic agonist properties and others, particularly those with an allyl group attached to a ring nitrogen, have opiate antagonist properties. It had been hoped that morphine part-structure research would produce a compound having both opiate agonist and antagonist properties since the opiate antagonist property would assure a user that the compound would have a greatly reduced dependance liability. Two recently marketed analgesics, pentazocine and phenazocine, have been found to be both antagonists and agonists although they still retain a certain degree of opiate dependance liability.

One potential morphine part-structure can be written as a decahydroisoquinoline with an hydroxyphenyl group substituted on a ring junction carbon atom para to the isoquinoline nitrogen. An attempt to prepare such a compound was described by Boekelheide in a paper appearing in J. Am. Chem. Soc., 69 790 (1947). This paper set forth the preparation of what, according to the numbering system then in vogue, were 10-phenyldecahydroisoquinolines. It was the author's conclusion, however, that the compound (IX) had a cis configuration and (footnote 5) showed low analgesic activity. The synthesis itself is cumbersome and not free from ambiguity. Sugimoto et. al., J. Pharm. Soc. Japan, 75 177 (1955), C.A. 1956 1814b described the synthesis of 8 or 10-alkylated decahydroquinolines. The reference also shows the morphine part-structure, 10-)m-hydroxyphenyl)-3-methylisoquinoline [presently named as 1-methyl-3a-(m-hydroxyphenyl)-1,2,3,3a,4,5,6,7,7a,8-decahydroisoquinoline] but without furnishing a synthesis for it. These authors do not, in fact, describe the preparation of any decahydroisoquinoline, but describe only the preparation of the decahydroquinoline analogs.

Belgian Pat. No. 802,577 issued Jan. 19, 1974, discloses a general method of preparing N-substituted 3a-phenyl, decahydroisoquinolines and specifically discloses 3a-phenyl-3a-(m-methoxy phenyl) and 3a-(m-hydroxyphenyl)-1-methyldecahydroisoquinolines, 3a-(m-methyoxyphenyl) and 3a-(m-hydroxyphenyl)-1-phenethyldecahydroisoquinolines, and 1-cyclohexylmethyl-3a-phenyldecahydroisoquinoline.

SUMMARY OF THE INVENTION

This invention provides decahydroisoquinolines of Structure I below:

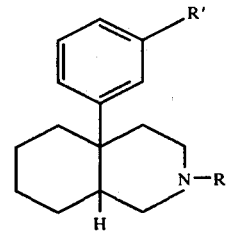

wherein
R is cyclopropylmethyl or cyclobutylmethyl;
R' is O-alk, OH, or

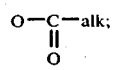

and
alk is (C₁-C₃) alkyl.

A preferred group of compounds of this invention are those in which R' is O-alk or OH and a particularly preferred group are those in which R' is OH only.

Also included within the scope of this invention are pharmaceutically-acceptable acid addition salts of the above bases formed with non-toxic acids. The term (C₁-C₃) alk, for which alk is the symbol, includes methyl, ethyl, isopropyl and n-propyl; thus, the term O-alk includes methoxy, ethoxy and the like. Similarly,

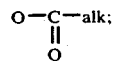

includes acetoxy, propionoxy and butyroxy.

The pharmaceutically acceptable salts of the amine bases represented by the above formula are formed with non-toxic acids, as for example, salts derived from inorganic acids such as: hydrochloric acid, nitric acid, phosphoric acid, sulfuric acid, hydrobromic acid, hydriodic acid, nitrous acid, phosphorous acid and the like, as well as salts derived from non-toxic organic acids including aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monhydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonates, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

boxyethyl)-2-(m-methoxyphenyl) cyclohexanone. The free acid thus formed is reacted with ethyl chloroformate in the presence of triethylamine to yield are acid anhydride which is in turn reacted with sodium azide. The product of this reaction, an acyl azide, is decomposed under conditions which promote the Curtius rearrangement to yield an isocyanate which, upon refluxing with aqueous acid, yields an amine of Structure III. This reaction sequence is illustrated below:

Reaction Sequence 1

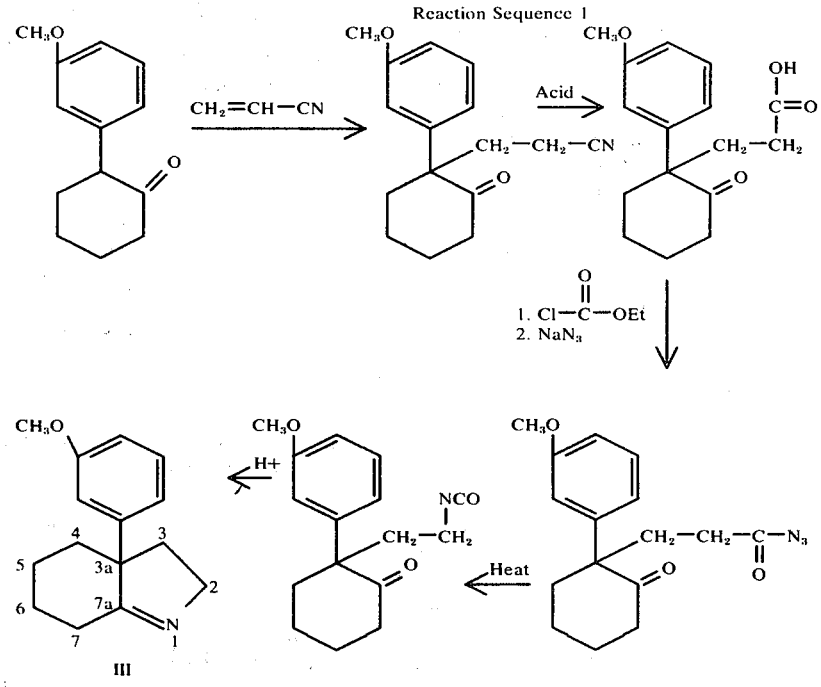

The bridgehead substituents, the meta-substituted phenyl at 3a and the hydrogen at 7a, can have either a cis or trans relationship to one another; i.e., the two substituents can be on the same "side" of the decahydroisoquinoline ring system (cis) or on the opposite "side" (trans). In addition, both the 3a and 7a carbon atoms are asymmetric, thus giving rise in each compound to 4 optical isomers, occuring as two racemates designated as the cis-dl and the trans-dl-pair Structure I is thus intended to comprehend both the optical isomers, the cis-dl and trans-dl racemates, and their individual enantiomorphs since, as far as is known, all of the individual isomers and isomer mixtures are useful as analgesic agonists or as analgesic antagonists; albeit large quantitative differences in analgesic agonist or antagonistic potency may exist between individual isomers or racemates. We prefer, however, those compounds according to structure I above which are in the trans configuration; i.e., the trans-dl racemic pair and the individual trans isomers such as the trans-l compound.

The compounds of this invention are prepared according to the following procedure using the synthesis of compounds in which R' is methoxyl for purely exemplarly purposes:

2-(2-Cyanoethyl)-2-(m-methoxyphenyl) cyclohexanone, prepared by the method of Boekelheide, J. Am. Chem. Soc., 69, 790 (1947), is hydrolysed to 2-(2-car- In carrying out the chemical transformations delineated in Reaction Sequence 1, we prefer to hydrolyze the nitrile function of 2-(β-cyanoethyl)-2-(m-methoxyphenyl)cyclohexanone using a mineral acid in a strongly acidic medium; for example, 12N aqueous hydrochloric acid in 60–70 percent aqueous acetic acid. Other mineral acids such as sulfuric and phosphoric may also be used, as can a purely aqueous reaction medium, without affecting the yield or purity of the product in any way. Alkaline hydrolysis may also be used, but it is necessary to use somewhat more stringent reaction conditions in order to carry the hydrolysis past the intermediate amide stage to the salt of the free acid. Higher boiling inert solvents such as diethyleneglycol can be used. The second step of the reaction sequence, the formation of an acid chloride or anhydride from the carboxylic acid of the previous step, can be accomplished by use of any of the milder chlorinating agents, for example, oxalyl chloride, thionyl chloride and the like to form an acid chloride or ethyl chloroformate to form an acid anhydride. We prefer to use ethyl chloroformate. An acid acceptor such as triethylamine can also be used to advantage in forming the desired acid chloride or anhydride, using an inert solvent. The reaction of the thus formed acid chloride with sodium azide to form the acid azide is carried out under standard conditions. It should be recognized however, that an alternate procedure for preparing the azide exists; i.e., the formation of the hydrazide by reaction of anhydrous hydrazine with the acid chloride followed by azide formation with nitrous acid. Rearrangement of the azide under Curtius rearrangement conditions, consisting simply in heating the azide, however synthesized, at the reflux temperature of benzene or toluene for from 1 to about 24 hours, yields the expected isocyanate. Acidification of the isocyanate product yields directly a 3H-indole (III). The acidification is carried out by heating the isocyanate with a concentrated mineral acid as for example hydrochloric or sulfuric acid for from 12–24 hours. The product, as the free base, is isolated by basifying the acid reaction medium with, for example, sodium hydroxide, sodium carbonate or the like.

The trans-dl-racemate (VI), is the predominant racemate isolated from this reaction with only minor quantities of the cis-dl-racemate (VIa) being found. Platinum hydrogenation also yields predominantly the trans-dl-racemate. On the other hand, hydrogenation of the enamine (Va) with 5 percent palladium-on-carbon yields a mixture of the cis-dl- and trans-dl 1 racemates (40–60), which racemates are readily separated from each other by precipitating the trans-dl racemate as a picrate salt. The cis-dl racemate does not form an insoluble picrate. The above series of reactions is illustrated below in Reaction Sequence 2:

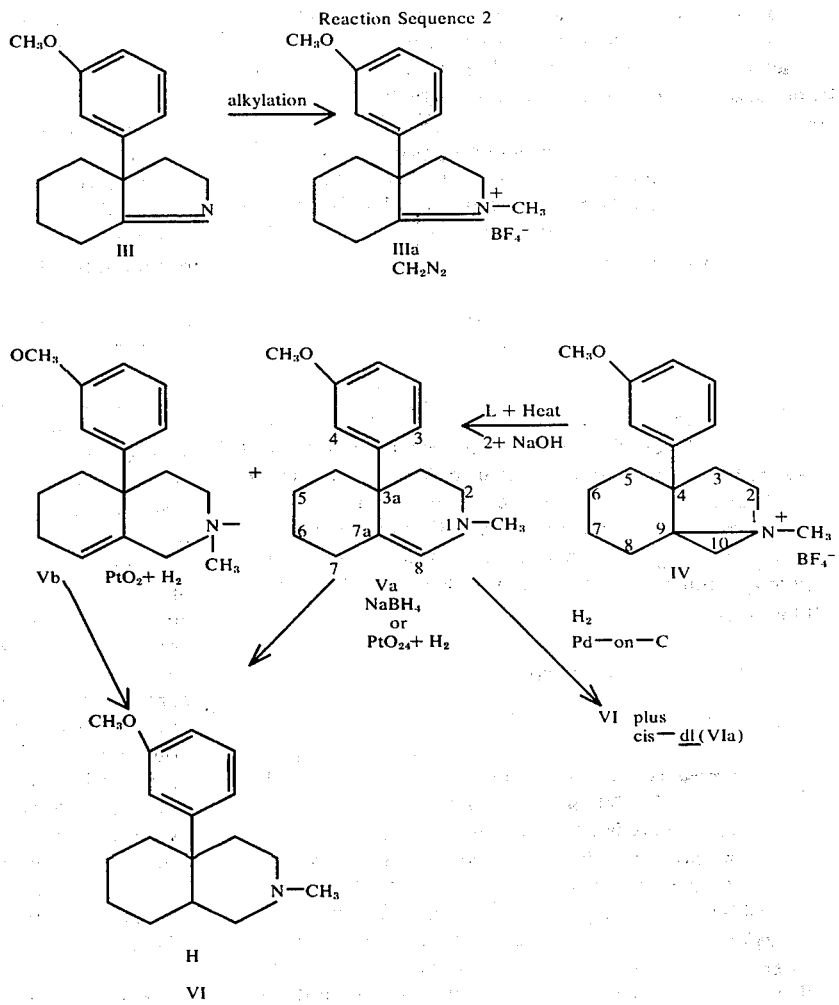

Structure III above is named 3a-(m-methoxyphenyl)-3H-indole or 3a-(m-methoxyphenyl)-3H-benzo[b]pyrrole and was prepared by Langlois et al. *Tetrahdron*, 27, 6541 (1971) using a different method of synthesis. Reaction Sequence 2 below outlines the production of the compounds of this invention represented by Structure I, from the intermediates of Reaction Sequence 1. The 3H-indole (III) end product of Reaction Sequence 1 is methylated quantitatively to yield an iminium salt (IIIa) which compound is next reacted, also quantitatively, with diazomethane to yield an aziridinium salt (IV). The aziridinium salt rearranges to produce a mixture of double-bond isomers (Va and Vb). Reduction of the enamine isomer (Va) with sodium borohydride in acetic acid yields a decahydroisoquinoline-VI or VIa-(I above in which R' is methoxy).

In carrying out the procedures outlined in Reaction Sequence 2 above, alkylation of the 3H-indole (III) to yield the quaternary methyl derivative (IIIa) is carried out preferably by treating the indole with trimethyloxonium tetrafluoroborate. Other alkylating agents can, however, be used as for example dimethyl sulfate, methyl iodide and the like. The product of this methylation reaction, an iodide or sulfate salt, is then metathesized to the fluoroborate salt by reaction with fluoroboric acid. Transformation of this quaternary salt to an aziridinium salt (IV) named systematically as a salt of 1-azonia-1-methyl-4-phenyl (or meta-substituted phenyl tricyclo [4,2,1,0$^{1-9}$] decane), is accomplished by reacting the iminium salt with diazomethane. The diazomethane can be generated in situ or added as a solution in accordance with procedures long established in the art. The aziridinium salt is rearranged to yield a mixture of double-bond isomers (Va and Vb) (85–15) by heating, preferably for about 1 hour at about 200° C. although longer reaction times at somewhat lower temperatures will give essentially the same yields. The direct product of the rearrangement is an amine salt which must be treated with a base such as sodium hydroxide or sodium carbonate in order to provide the thus produced N-methyl octahydroisoquinolines (Va and Vb) as free bases. The reduction of the (Va and Vb) to the corresponding decahydroisoquinolines (VI and VIa) has been discussed above.

Compounds according to structure VI or VIa containing a meta-hydroxyphenyl substituent at C-3a are prepared from the corresponding methoxy compound by dealkylation using, for example, hydrobromic acid in acetic acid.

The preparation of compounds according to Formula I can be accomplished by several procedures. As a starting point, the N-methyl derivative (VI above) can be reacted with phenylchloroformate to yield a carbamate (I wherein R is

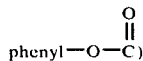
phenyl—O—C)

Hydrolysis of this carbamate provides the secondary amine (I wherein R is H). Alkylation of the secondary amine by standard procedures using a suitable cycloalkyl halide readily yields the compounds of the invention according to I above wherein R is as defined.

Alternatively, an amide can be formed with the secondary amine function (I wherein R is H) with an acylating agent

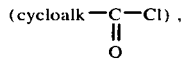
(cycloalk—C—Cl),
 ||
 O and the resulting amide reduced to a tertiary amine function with LiAlH$_4$ or other similar reducing agent, to yield compounds according to I.

Compounds according to I above in which R' is O-alk, alk being other then methyl, can be prepared either by employing as a starting material a 2-(2-cyanoethyl)-2-(m-alkoxyphenyl) cyclohexanone in which the alkoxy group is ethoxy or propoxy, or can be derived from the m-hydroxyphenyl derivative by any standard phenolic ether synthesis.

Compounds according to I above in which R' is

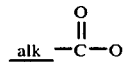
alk —C—O are prepared by standard acylation procedures from the corresponding compound in which R' is OH, such acylation procedures involving, for example, the reaction of an anhydride

( alk —C)$_2$O, a mixed anhydride,

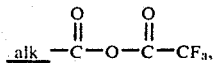
alk —C—O—C—CF$_3$, or an acid chloride

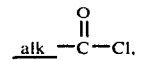
alk —C—Cl, with the phenol or preferably, an alkali metal salt thereof.

This invention is further illustrated by the following specific examples.

EXAMPLE 1

A mixture was prepared containing 368 g. of 2-(β-cyanoethyl)-2-(m-methoxyphenyl)cyclohexanone, 2000 ml. of glacial acetic acid 850 ml. of 12 N aqueous hydrochloric acid and 850 ml. of water. The mixture was refluxed for about 19 hours and then cooled to room temperature. Sufficient ice and water were added to make a volume of about 11 liters. The resulting mixture was stirred for about 30 minutes at which point a precipitate comprising 2-(β-carboxyethyl)-2-(m-methoxyphenyl) cyclohexanone formed. The supernate was removed by centrifugation, and the precipitate collected. The precipitate was thoroughly washed with water and then dried to yield about 280 g. of 2-(β-carboxyethyl)-2-(m-methoxyphenyl)cyclohexanone melting at about 143–4° C. after recrystallization from water.

About 255 g. of 2-(β-carboxyethyl)-2-(m-methoxyphenyl)-cyclohexanone were mixed with 125 g. of triethylamine and about 20 g. of sodium sulfate. A solution of 99 g. of ethyl chloroformate in 3250 ml. of anhydrous ether was added in dropwise fashion, thus converting the carboxyethyl group to an acid anhydride. The reaction mixture was stirred for about 1 hour at about 0° C. at which point 89 g. of sodium azide in 350 ml. of water were added in dropwise fashion. After the addition had been completed, the reaction mixture was stirred for an additional two hours at 0° C. The organic layer was separated. 2-(β-Azidoformylethyl)-2-(m-methoxyphenyl)cyclohexanone formed in the above reaction was isolated as an oil by evaporation of the ether in vacuo. The residual oil was dissolved in 3.5 l. of benzene, and the solution heated at refluxing temperature for about 1.5 hours. The benzene was removed by evaporation in vacuo. By this procedure the azidoformyl group was rearranged under Curtius conditions to yield the corresponding isocyanate. The benzene was removed by evaporation in vacuo. The residual isocyanate was next hydrolyzed to the cyclic imine by heating overnight in a mixture containing 1200 ml. of water, 1200 ml. of glacial acetic acid and 1200 ml. of 12N aqueous hydrochloric acid. The hydrolysis mixture was cooled and then made strongly basic with 50 percent aqueous sodium hydroxide. 3a-(m-Methoxyphenyl)-2,3,3a,4,5,6,7-heptahydroindole thus procuced was extracted into ether, and the ether layer separated, washed with water and dried. Evaporation of the ether layer to dryness yielded 153.2 g. of 3a-(m-methoxyphenyl)-2,3,3a,4,5,6,7-heptahydroindole, distilling at about 140° C. at 0.07 mm/g. (For comparison, see Langlois et. al., *Tetrahedron*, 27, 5641

(1971) compound 10 and page 5647, table 4, compound 42).

About 341 g. of 3a-(m-methoxyphenyl)-2,3,3a,4,5,6,7-heptahydroindole were dissolved in 600 ml. of methyl ethyl ketone. 184 g. of dimethyl sulfate were added to this solution in dropwise fashion. The reaction mixture was heated at refluxing temperature for 1 hour. 1100 ml. of water were then added over a one-half hour period and the reaction mixture refluxed for another 3 hours. The reaction mixture was made strongly basic with 50 percent aqueous sodium hydroxide with external cooling provided. 1-Methyl-3a-(m-methoxyphenyl)-1,2,3,3a,4,5,6-heptahydroindole formed in the above reaction, being insoluble in the alkaline layer, separated and was extracted into ether. The ether extract was separated, washed with water and dried. Evaporation of the ether in vacuo left a residual oil comprising 1-methyl-3a-(m-methoxyphenyl)-1,2,3,3a,4,5,6heptahydroindole boiling at about 144° C. at 0.4 mm/Hg; yield = 325.4 g.

325.4 g. of 1-methyl-3a-(m-methoxyphenyl)-1,2,3,3a, 4,5,6-heptahydroindole were dissolved in 2500 ml. of ether. A 50 percent mixture of 50 percent fluorboric acid and anhydrous ethanol was added in dropwise fashion with stirring until the solution was acid to congo red. The ether layer was separated by syphoning. The aqueous layer which contained 1-methyl-3a-(m-methoxyphenyl)-2,3,3a,4,5,6,7-heptahydroindolinium fluoborate formed in the above reaction was allowed to stand while the fluoborate salt slowly crystallized. The salt was collected by filtration, and the filter cake washed with ether. The filter cake was then triturated with an anhydrous ethanol-ether solvent mixture. The solvent was separated by filtration, and the filter cake was dried. Yield of the fluoroborate salt was about 392 g.

A solution of 55 g. of 1-methyl-3a-(m-methoxyphenyl)- 2,3,3a,4,5,6,7-heptahydroindolinium fluoborate in 500 ml. of methylene chloride was cooled to about 0° C. A solution of diazomethane prepared from 103 g. of N-methyl-N-nitroso-p-toluenesulfonamide in ether was added over a 5-hour period. The reaction mixture was allowed to warm to room temperature and was stirred overnight. The supernate was separated from the precipitated oil comprising the fluoboroate salt of the corresponding aziridinium compound, 1-azonia-1-methyl-4-(m-methoxyphenyl)tricyclo[4,2,1,0$^{2-8a}$] decane. The oily residue was triturated with three 1000 ml. portions of ether, and the ether washes were discarded. The residual oil was transferred to a 500 ml. round-bottom flask and heated at atmospheric pressure for about 1 hour at 200° C., thus forming 1-methyl-3a-(m-methoxyphenyl)-1,2,3,3a,4,5,6,7-octahydroisoquinoline, which compound was dissolved in anhydrous ethanol, and the ethanol solution treated with an excess of 50 percent aqueous sodium hydroxide and water. The octahydroisoquinoline, being insoluble in the alkaline solution, separated and was extraced into ether. The ether extract was separated and dried, and the ether removed therefrom by evaporation in vacuo. 1-methyl-3a-(m-methoxyphenyl)-1,2,3,3a,4,5,6,7-octahydroisoquinoline thus prepared distilled at about 168° C. at 0.5 mm/hg.

A mixture was prepared containing about 163 g. of 1-methyl-3a-(m-methoxyphenyl)-1,2,3,3a,4,5,6,7-octahydroisoquinoline, 90 g. of sodium borohydride and 4500 ml. of tetrahydrofuran was cooled to about 5° C. 1630 ml. of acetic acid were added in dropwise fashion while maintaining the temperature below about 10° C. The mixture was stirred for one-half hour at about 5° C. and then gradually warmed to refluxing temperature with mild heating. The mixture was refluxed for 1 hour, and was then made strongly basic with about 3 liters of 25 percent aqueous sodium hydroxide. The tetrahydrofuran layer was decanted, and the aqueous layer washed with three 2-liter portions of ether. The ether and tetrahydrofuran layers were combined and evaporated to dryness in vacuo. The resulting residue, comprising 1-methyl-3a-(m-methoxyphenyl)-1,2,3,3a,4,5,6,7,7a,8-decahydroisoquinoline formed in the above reaction was dissolved in about 3.5 l of ether, and the ethereal layer washed with three 2 l. portions of water. The ether layer was dried, and the ether removed therefrom by evaporation to dryness in vacuo. The yield of the decahydroisoquinoline was 162.3 g.

The compound was purified via the picrate salt which was converted back to the free base by refluxing the salt with saturated lithium hydroxide at the ratio 30 g. of picrate to 1000 ml. of saturated aqueous lithium hydroxide solution. Extraction of the free base into benzene followed by distillation of the base yielded 1-methyl-3a-(m-methoxyphenyl)-1,2,3,3a, 4,5,6,7,7a,8-decahydroisoquinoline boiling in the range 145–79° C. at 0.1 mm/Hg. The corresponding picrate salt melted at about 161–2° C. after recrystallization from aqueous ethanol. Overall yield through the sodium borohydride reduction procedure was about 90 percent.

Alternatively, 1-methyl-3a-(m-methoxyphenyl)-1,2,3,3a,4,5,6,7-octahydroisoquinoline was reduced over platinum oxide with hydrogen to yield the corresponding decahydroisoquinoline. 66.7 g. of the octahydro compound were dissolved in 650 ml. of absolute ethanol. 5 g. of platinum oxide catalyst were added, and the hydrogenation mixture subjected to 60 psi of hydrogen. The yield of 1-methyl-3a-(m-methoxyphenyl)-1,2,3,3a,4,5,6,7,7a,8-decahydroisoquinoline synthesized by this procedure was about 96 percent. The compound was again isolated as the picrate salt.

The 1-methyl group was cleaved from the above decahydroisoquinoline by dissolving 8 g. of 1-methyl-3a-(m-methoxyphenyl)-1,2,3,3a,4,5,6,7.7a,8-decahydroisoquinoline in 64 ml. of methylene chloride and adding thereto a solution of 5.6 g. of phenyl chloroformate in 16 ml. of methylenechloride. The resulting mixture was refluxed for about 2 hours, and allowed to stand overnight. The solvents were then evaporated in vacuo. 100 ml. of 5 percent aqueous sodium hydroxide were added, and the resulting mixture stirred with warming for about 15 minutes. 1-Phenylcarboxy-3a-(m-methoxyphenyl)-1,2,3,3a,4,5, 6,7,7a,8-decahydroisoquinoline formed in the above reaction, being insoluble in the basic layer, separated and was extracted into ether. The ether extract was separated and washed with water. The ether extract was in turn extracted with 250 ml. of 10 percent aqueous hydrochloric acid followed by 250 ml. of water to remove any unreacted N-methyldecahydroisoquinoline. The ether layer was separated, dried, and the ether removed by evaporation. The residue was refluxed for 66 hours in 240 ml. of anhyrous ethanol and 50 ml. of 50 percent aqueous potassium hydroxide. The volatile constituents were removed in vacuo and the resulting concentrate extracted with ether. The ether extract was separated and dried. Evaporation of the ether left a residue comprising 1-phenylcarboxy-3a-(m-methoxyphenyl)-1,2,3,3a,4,5,6,7,7a,8-decahydroisoquinoline which was dissolved in 250 ml. of 10 percent aqueous hydrochloric acid. The acid layer was washed with ether, and the ether wash was discarded. The aqueous layer was made strongly basic with 50 percent sodium hydroxide, and 3a-(m-methoxyphenyl)-1,2,3,3a,4,5,6,7,7a,8-decahydroisoquinoline thus formed was extracted into ether. The ether layer was separated, dried and the ether removed therefrom by evaporation. Distillation of the resulting residue yielded 5.5 g. of a 3a-(m-methoxyphenyl)-1,2,3,3a,4,5,6,7,7a,8-decahydroisoquinoline boiling at about 148° C. at 0.2 mm/Hg.

3a-(m-methoxyphenyl)-1,2,3,3a,4,5,6,7,7a,8-decahydroisoquinoline was converted to the corresponding 3a-(m-hydroxyphenyl) derivative by treatment with 50 percent HBr in 50 percent aqueous acetic acid. In this procedure, 5.2 g. of freshly distilled 3a-(m-methoxyphenyl)-1,2,3,3a,4,5,6,7,7a,8-decahydroisoquinoline were dissolved in 40 ml. of 50 percent aqueous hydrobromic acid and 40 ml. of 50 percent aqueous a-(m-Hydroxyphenyl-acid. The resulting mixture was refluxed for 18 hours. The reaction mixture was cooled, diluted with about 250 ml. of water and the pH thereof adjusted to about 10.4 with 50 percent aqueous sodium hydroxide. The reaction mixture was treated with a 3:1 n-butanol-benzene solvent system. 3a-(m-Hydroxyphenyl)-1,2,3,3a,4,5,6,7,7a,8-decahydroisoquinoline being insoluble in the alkaline layer passed into the organic layer. The organic layer was separated and dried, and the solvents removed therefrom by evaporation in vacuo. 5 g. of 3-(m-Hydroxyphenyl-1,2,3,3a,4,5,6,7,7a,8-decahydroisoquinoline were obtained which melted at about 212°–214° C. with decomposition after recrystallization from dimethylformamide.

Analysis:Calc.: C, 76.67; H, 9.65; N, 6.39.
Found: C, 76.88; H, 9.35; N, 6.24.

EXAMPLE 2

Ten grams of 3a-(m-hydroxyphenyl)-1,2,3,3a,4,5,6,7,7a,8-decahydroisoquinoline and 11.7 ml. of triethylamine were dissolved in 170 ml. of dimethylformamide. 11.4 g. of cyclopropylcarbonyl chloride were added to this solution in dropwise fashion. The resulting mixture was heated in the range 65–80° C. for about 2 hours, was cooled, and was the poured into about 1000 ml. of water. 1-cyclopropylcarbonyl-3a-(m-hydroxyphenyl)-1,2,3,3a,4,5,6,7,7a,8-decahydroisoquinoline formed in the above reaction was extracted therefrom with three 1000 ml. portions of ether. The ether extracts were combined and washed with three 300 ml. portions of saturated aqueous sodium chloride followed by one 200 ml. water wash. The ether layer was separated, and dried, and the ether removed therefrom by evaporation in vacuo. The dried residue was dissolved in 100 ml. of THF (tetrahydrofuran) and this solution added dropwise to a solution of 6.5 g. of lithium aluminumhydride in 300 ml. of THF. After the addition had been completed, the reaction mixture was heated to reflux for about 4 hours. Next, about 75 ml. of ethyl acetate were added to react with any excess lithium aluminumhydride present. Saturated ammonium tartrate was added to decompose inorganic salts present and to cause them to coagulate. The THF solution was separated by decantation, and the residual salts washed with three 500 ml. portions of THF. The THF washes were combined with the original THF layer, and the solvent removed by evaporation to dryness in vacuo. The residual product comprising 1-cyclopropylmethyl-3a-(m-hydroxyphenyl)-1,2,3,3a,4,5,6,7,7a,8-decahydroisoquinoline formed in the above reaction was dissolved in 3 l. of ether. The ether solution was washed with three 350 ml. portions of saturated sodium chlorides solution aqueous followed by a 300 ml. water wash. The ether layer was separated, dried and the ether removed by evaporation in vacuo. Addition of ethyl acetate to the residual oil produced crystals of 1-cyclopropylmethyl-3a-(m-hydroxyphenyl)-1,2,3,3a,4,5,6,7,7a,8-decahydroisoquinoline which melted at about 164–6° C. after recrystallization from ethyl acetate.

Analysis: Calc. for $C_{19}H_{27}NO$;
C, 79.97; H, 9.54; N, 4.91.
Found: C, 79.72; H, 9.63; N, 4.62.

The maleate salt was prepared from the free base: m.p. 146–8° C.
Analysis: Calc. for $C_{23}H_{31}NO_5$:
C, 68.80; H, 7.78; N, 3.49.
Found: C, 68.52; H, 7.80; N, 3.68.

Other compounds of this invention prepared by the above procedure include: 1-cyclobutylmethyl-3a-(m-hydroxyphenyl)-1,2,3,3a,4,5,6,7,7a,8-decahydroisoquinoline maleate: m.p. 136–8° C.
Analysis: Calc. for $C_{24}H_{33}NO_5$; C, 69.37; H, 8.01; N, 3.33.
Found: C, 69.19; H, 7.79; N, 3.08.

1-Cyclopropylmethyl-3a-(m-methoxyphenyl)-1,2,3,3a,4, 5,6,7,7a,8-decahydroisoquinoline maleate: m.p. 93–5° C.
Analysis: Calc. for $C_{24}N_{33}NO_5$;
C, 69.37; H, 8.01; N, 3.33.
Found: C, 69.17; H, 7.96; N, 3.29.

As previously stated, the compounds of this invention represented by formula I above contain two asymmetric centers, at 3a and 7a. Thus the compounds can exist as four diastereoisomers occuring as two racemic pairs, commonly designated as the cis-dl and the trans-dl racemates.

The preparation of optically-active isomers of compounds according to Structure I, are illustrated below.

EXAMPLE 3

Thirty six and two-tenths grams of 1-methyl-3a-(m-methoxyphenyl)-1,2,3,3a,4,5,6,7,7a,8-decahydroisoquinoline and 23.4 g. of L(+)-mandelic acid were dissolved in 100 ml. of isopropanol. The solvent was removed by evaporation and the residue recrystallized from 1000 ml. of water. The resulting precipitate weighing 21.1 g. was separated by filtration and recrystallized from a mixture of 28 percent acetone and 72 percent isopropyl ether. A sample of the mandelate salt was treated with an excess of 1N sodium hydroxide. Trans-l(−)-1-methyl-3a-(m-methoxyphenyl-1,2,3,3a,4,5,6,7,7a,8-decahydrolisoquinoline being insoluble in the aqueous alkaline layer separated and was extracted into ether. The ether was evaporated and the rotation of the residual free base obtained by standard procedures. The recrystallization of the L(+)-mandelate salt above from 28 percent acetone-72 percent isopropyl ether continued until the samples of the Trans-l(−)-1-methyl-3a-(m-methoxyphenyl)-1,2,3,3a,4,5,6,7,7a,8-decahydrolisoquinoline showed a constant rotation after repeated recrystallization. Trans-l(−)-1-methyl-3a-(m-methoxyphenyl)-1,2,3,3a,4,5,6,7,7a,8-decahydrolisoquinoline thus prepared had a rotation of $[\alpha]_{350}^{25°} = -48.1°$. L(+)-mandelate salt;

Analysis:cal.: C, 72.96; H, 8.08; N, 3.40.
Found: C, 72.67; H, 8.21; N, 3.23.

The above procedure was repeated using D(−) mandelic acid in place of L(+)-mandelic acid in the above procedure. Trans-d(−)-1-methyl-3a-(m-methoxyphenyl)-1,2,3,3a,4,5,6,7,7a,8-decahydrolisoquinoline thus obtained had the following rotation: $[\alpha]_{350}^{25°} = +47.6°$.

Following the procedure of Example 1 both the trans-l (+)-and trans-d(−)-1-methyl-3a-(m-methoxyphenyl)-1,2,3,3a,4, 5,6,7,7a,8-decahydroisoquinoline isomers were N-demethylated and O-demethylated to yield respectively trans-l(+) and trans-d(-)-3a-(m-hydroxyphenyl)-1,2,3,3a,4,5,6,7,7a,8-decahydroisoquinoline isomers. N-acylation of the individual isomers with cyclopropylcarbonyl chloride followed by reduction of the resulting amides with LiAlH$_4$ by the procedure of Example 2 yielded trans-l(−)-1-cyclopropylmethyl-3a-(m-hydroxyphenyl)-1,2,3,3a,4,5,6,7,7a,8-decahydrolisoquinoline, maleate salt: m.p. 197.°–109° C.: $[\alpha]_{350}^{25°} = -12.7$; $[\alpha]_d^{25°} = -3.8$, Analysis Calc.: C, 68.80; H, 7.78; N, 3.48;
Found: C, 68.70; H, 7.62; N, 3.31.

Trans-d(+)-1-cyclopropylmethyl-3a-(m-hydroxyphenyl)-1,2,3,3a,4,5,6,7,7a,8-decahydrolisoquinoline, maleate salt. m.p. 109.5°–110° C. $[\alpha]_{350}^{25°} = +16.2$; $[\alpha]_d^{25°} = +5.9$.

Analysis:Calc.: C, 68.80; H, 7.78; N, 3.49;
Found: C, 68.56; H, 7.62; N, 3.26.

trans-l(−)-1-Cyclopropylmethyl-3a-(m-methoxyphenyl)-1,2,3,3a,4,5,6,7,7a,8-decahydroisoquinoline and its trans-d(+) isomer are prepared by the procedure of Example 2 from the corresponding trans-l(−) and trans-d(+)-3a-(m-methoxyphenyl)-1,2,3,3a,4,5,6,7,7a,8-decahydroisoquinolines which are in turn prepared by N-demethylation only of the trans-l(+) and trans-d-(−)-1-methyl-3a-(m-methoxyphenyl)-1,2,3,3a,4,5,6,7,7a,8-decahydroisoquinoline isomers provided by the procedure of Example 1.

Optically active isomers of the cis-dl-series; i.e., cis-d-(+)-1-cyclobutyl-3a-(m-methoxyphenyl)-1,2,3,3a,4,5,6,7,7a,8-decahydroisoquinoline, cis-l(−)-1-cyclopropylmethyl-3a-(m-hydroxyphenyl)-1,2,3,3a,4,5,6,7,7a,8-decahydroisoquinoline and the like as well as the trans-dl-1-cyclobutyl isomers are prepared in an entirely analogous fashion.

EXAMPLE 4

Preparation of Salts

Salts of the free bases of this invention, other than the mandelate or maleate salts whose preparation is illustrated above, are prepared by dissolving the free base in ether and adding an equivalent of a suitable non-toxic acid, also in ether. The salts thus formed, as for example the sulfate and phosphate salts, are insoluble in ether and can be isolated by filtration. Alternatively, the amine base can be dissolved in ethanol and an equivalent of the acid added as an ethanolic solution. In this instance, since the salts thus formed are soluble in the reaction mixture, they are isolated by evaporation of the solvent in vacuo. Salts which can be formed by the above procedure include the hydrochloride, sulfate, hydrobromide, phosphate, hydrogen phosphate, dihydrogen phosphate, acetate, maleate, succinate, tartrate, citrate, benzoate, and p-toluene sulfonate salts of the N-cycloalkylmethyl 3a-(m-hydroxyphenyl)-1,2,3,3a,4,5,6,7,7a,8-decahydroisoquinolines of this invention and the corresponding m-alkoxy and m-acyloxy derivatives.

As previously stated, the compounds of this invention have both opiate-agonist and opiate-antagonist properties. While the compounds are capable of producing analgesia in mammals, the added characteristic of being simultaneously opiate-antagonists greatly decreases the physical dependence (addiction) liability of the particular drug. It might be said that the opiate-antagonist activity of the compounds of this invention acts as a built-in safety device tending to mitigate any physical dependence-inducing (addictive) properties of the drug caused by its opiate-like analgesic action.

The compounds of this invention demonstrate their analgesic activity in the mouse-writhing test and in the rat tail jerk assay, both standard pharmalcological assays for analgesic action. For example, the compounds of this invention have demonstrated activity in inhibiting writhing in mice induced by the intraperitoneal injection of acetic acid and Table 1 below sets forth the results of this assay. In the Table, column 1 gives the name of the compund; column 2, the dosage in mg./kg. of mouse weight; column 3, the route of administration of the drug ("S.C." is subcutaneous and "or" is oral); and column 4, the percent inhibition found at the particular dose level. All readings were made at 0.5 hours. Median inhibiting doses (I.D.$_{50}$) are also included in the Table.

Table 1

| Name of Compound | Dose | Route | % Inhibition |
| --- | --- | --- | --- |
| Trans-dl-1-cyclobutylmethyl-3a-(m-hydroxyphenyl)-1,2,3,3a,4,5,6,7,7a,8-decahydroisoquinoline maleate | 100 | S.C. | 100 |
|  | 20 | S.C. | 100 |
|  | 2 | S.C. | 96 |
| I.D.$_{50}$ S.C. 1.0 mg./kg. | 1 | S.C. | 46 |
|  | 100 | or | 100 |
|  | 20 | or | 36 |
| Trans-dl-1-cyclopropylmethyl-3a-(m-methoxyphenyl)-1,2,3,3a,4,5,6,7,7a,8-decahydroisoquinoline maleate | 100 | S.C. | 100 |
|  | 20 | S.C. | 64 |
|  | 10 | S.C. | 20 |
| I.D.$_{50}$ S.C. = 10–20 mg./kg. | 100 | or* | 89 |
| or = 20–50 mg./kg. | 50 | or | 69 |
|  | 50 | or* | 79 |
|  | 100 | or | 87 |
|  | 20 | or | 13 |
|  | 20 | or* | 5 |
| Trans-dl-1-cyclopropylmethyl-3a-(m-hydroxyphenyl)-1,2,3,3a,4,5,6,7,7a,8-decahydroisoquinoline maleate | 100 | S.C. | 100 |
|  | 20 | S.C. | 99 |
|  | 10 | S.C. | 72 |
| I.D.$_{50}$ S.C. = 2–5 mg./kg. | 5 | S.C. | 66 |
| or = 20–50 mg./kg. | 2 | S.C. | 6 |
|  | 100 | or | 92 |

Table 1-continued

| Name of Compound | Dose | Route | % Inhibition |
|---|---|---|---|
|  | 50 | or | 56 |
|  | 20 | or | 46 |
| Trans-dl-1-cyclopropylmethyl-3a-(m-hydroxyphenyl)-1,2,3,3a,4,5,6,7,7a,8-decahydroisoquinoline (free base) I.D.$_{50}$ S.C. = 2-5 mg./kg. | 5 | S.C.* | 70 |
|  | 2 | S.C.* | 43 |
| Trans-d(+)-1-cyclopropylmethyl-3a-(m-hydroxyphenyl)-1,2,3,3a,4,5,6,7,7a,8-decahydroisoquinoline maleate | 5 | S.C.* | inact |
|  | 50 | S.C.* | 44 |
|  | 100 | S.C.* | 51 |
| Trans-l(−)-1-cyclopropylmethyl-3a-(m-hydroxyphenyl)-1,2,3,3a,4,5,6,7,7a,8-decahydroisoquinoline maleate | 5 | S.C.* | 72 |
|  | 2 | S.C.* | 47 |

*Reading made at 0.25 hours

In all instances, the inhibitory action of the compounds in Table 1 in the mouse writhing test was blocked by the administration of naloxone except for compound 5, the trans-d(+) isomer, thus showing that the compounds are opiate-like analgesics.

The compounds of this invention are also active in the rat tail jerk assay, another standard pharmacologic test for analgesic activity of the opiate-type. Such activity is manifested as an increase in the reaction time of the animal in removing (jerking) its tail from a nearby heat stimulus (a resistance wire) after drug administration compared to control time (no drug administered). Table 2 which follows gives the increased reaction times over control times produced by the compounds of this invention when administered subcutaneously. Table 3 gives similar information for oral administration of the compounds. In Tables 2 and 3, column 1 gives the name of the compound; column 2, the dose; column 3, time of observation after administration of the drug; column 4, the increase in reaction time above control in seconds; and column 5, the level of significance of the results ("p" value). A reaction time of 30 seconds (approximately 24-25 sec. above control) is considered to be maximal. All drugs were administered as aqueous solutions. More than one value for a given dose level indicates multiple determinations. The results are not averaged.

Table 2

| Name of Compound | Subcutaneous Dose | Time of Observation (Minutes) | Increase in Reaction Time Over Control | "p" |
|---|---|---|---|---|
| Transd-dl-1-cyclobutylmethyl-3a-(m-hydroxyphenyl)-1,2,3,3a,4,5,6,7,7a,8-decahydroisoquinoline maleate | 0.25 mg./kg. | 30 | .71 | .02 |
|  | 0.5 mg./kg. | 30 | .21 | .4 |
|  | 1 mg./kg. | 10 | .46 | .05 |
|  |  | 30 | 1.63 | .001 |
|  |  | 60 | .17 | .5 |
|  | 2 mg./kg. | 10 | 2.17 | .001 |
|  |  | 30 | 2.50 | .001 |
|  |  | 60 | .96 | .01 |
|  | 10 mg./kg. | 10 | 17.88 | .001 |
|  |  | 30 | 23.04 | .001 |
|  |  | 60 | 22.13 | .001 |
| Trans-dl-1-cyclopropylmethyl-3a-(m-methoxyphenyl)-1,2,3,3a,4,5,6,7,7a,8-decahydroisoquinoline maleate | 80 mg./kg. | 30 | 1.75 | .02 |
|  |  | 120 | 1.05 | .1 |
| Trans-dl-1-cyclopropylmethyl-3a-(m-hydroxyphenyl)-1,2,3,3a,4,5,6,7,7a,8-decahydroisoquinoline maleate | 0.5 mg./kg. | 15 | .75 | .1 |
|  | 1 mg./kg. | 15 | .50 | .2 |
|  | 2 mg./kg. | 15 | 2.21 | .001 |
|  | 3 mg./kg. | 15 | 2.04 | .02 |
|  | 5 mg./kg. | 15 | 1.21 | .01 |
|  |  | 15 | 2.50 | .01 |
|  |  | 15 | 3.60 | .01 |
|  | 7 mg./kg. | 15 | 4.25 | .001 |
|  | 10 mg./kg. | 15 | 4.50 | .001 |
|  |  | 15 | 1.50 | .01 |
|  |  | 15 | 3.90 | .01 |
|  | 20 mg./kg. | 15 | 5.17 | .001 |
|  | 20 mg./kg. | 15 | 3.70 | .001 |
|  | 25 mg./kg. | 15 | 4.40 | .001 |
|  | 30 mg./kg. | 15 | 4.25* | .01 |
|  | 40 mg./kg. | 15 | 3.90 | .01 |
|  | 50 mg./kg. | 5 | 4.85** | .01 |
|  |  | 10 | 4.95** | .01 |
|  |  | 10 | 4.85* | .001 |
|  |  | 15 | 6.08* | .001 |
|  |  | 15 | 4.0 | .01 |
|  |  | 15 | 6.50** | .001 |
|  |  | 15 | 5.98 | .001 |
|  |  | 30 | 5.10** | .01 |
|  |  | 30 | 5.75 | .001 |
|  |  | 45 | 3.00 | .001 |
|  |  | 60 | 3.65 | .01 |
|  |  | 60 | 1.20 | .05 |
|  |  | 90 | 1.85 | .01 |
|  |  | 120 | 2.45 | .01 |
|  |  | 180 | 1.80 | .01 |

Table 2-continued

| | Subcutaneous | | | |
|---|---|---|---|---|
| Name of Compound | Dose | Time of Observation (Minutes) | Increase in Reaction Time Over Control | "p" |
| | 60 mg./kg. | 15 | 4.40* | .01 |
| | 100 mg./kg. | 15 | 4.15 | .01 |
| | 200 mg./kg. | 15 | 5.65 | .001 |
| Trans-d(+)-1-cyclopropylmethyl-3a- | 10 mg./kg. | 15 | 0 | |
| (m-hydroxyphenyl)-1,2,3,3a,4,5,6, | 50 mg./kg. | 15 | .25 | .5 |
| 7,7a,8-decahydroisoquinoline | | 30 | 1.30 | .01 |
| maleate | | 60 | 2.25 | .05 |
| | | 120 | .10 | .5 |
| | 100 mg./kg. | 15 | .50 | .1 |
| | | 30 | 1.55 | .02 |
| | | 60 | 3.50 | .01 |
| | | 120 | 1.15 | .05 |
| Trans-l(−)-1-cyclopropylmethyl- | 0.1 mg./kg. | 30 | 85 | .2 |
| 3a-(m-hydroxyphenyl)-1,2,3,3a,4, | 0.5 mg./kg. | 30 | 1.30 | .01 |
| 5,6,7,7a,8-decahydroisoquinoline | 1 mg./kg. | 30 | 0 | |
| maleate | 2 mg./kg. | 30 | 1.25 | .05 |
| | | 30 | 3.30 | .001 |
| | | 30 | 2.10 | .01 |
| | 5 mg./kg. | 10 | 2.75 | .01 |
| | | 15 | 3.45 | .01 |
| | | 30 | 3.55 | .001 |
| | | 30 | 2.95 | .001 |
| | | 30 | 6.65* | .001 |
| | | 30 | 6.95* | .001 |
| | | 60 | 1.0 | .05 |
| | | 120 | 0 | |
| | | 180 | 0 | |
| | 10 mg./kg. | 10 | 7.30* | .001 |
| | | 15 | 5.80 | .001 |
| | | 15 | 6.70* | .001 |
| | | 30 | 3.25 | .001 |
| | | 30 | 7.90 | .001 |
| | | 60 | 3.0 | .01 |
| | | 90 | 2.55 | .01 |
| | | 120 | 4.0 | .01 |
| | | 180 | 1.50 | .01 |
| | 50 mg./kg. | 15 | 7.35 | .001 |

*20 sec. cut off
**15 sec. cut off

Table 3

| | Oral | | | |
|---|---|---|---|---|
| Name of Compound | Dose | Time of Observation (Minutes) | Increase in Reaction Time Over Control | "p" |
| Trans-dl-1-cyclobutylmethyl-3a-(m-hydroxy- | 10 mg./kg. | 10 | .43 | .3 |
| phenyl)-1,2,3,3a,4,5,6,7,7a,8-decahydroiso- | | 30 | .63 | .01 |
| quinoline maleate | | 60 | .21 | .4 |
| | 25 mg./kg. | 30 | 1.71 | .001 |
| | | 60 | 1.04 | .01 |
| | 50 mg./kg. | 30 | 12.42 | .01 |
| Trans-dl-1-cyclopropylmethyl-3a-(m-methoxy- | 20 mg./kg. | 30 | 1.10 | .01 |
| phenyl)-1,2,3,3a,4,5,6,7,7a,8-decahydroiso- | | 120 | .20 | .5 |
| quinoline maleate | 80 mg./kg. | 30 | 8.05 | .2 |
| | | 120 | 1.19 | .05 |
| Trans-dl-1-cyclopropylmethyl-3a-(m-hydroxy- | 5 mg./kg. | 15 | 0 | |
| phenyl)-1,2,3,3a,4,5,6,7,7a,8-decahydroiso- | 10 mg./kg. | 15 | .90 | .2 |
| quinoline maleate | 15 mg./kg. | 15 | .95 | .05 |
| | 20 mg./kg. | 15 | 1.45 | .01 |
| | | 15 | .54 | .2 |
| | | 30 | 1.17 | .01 |
| | | 45 | 1.33 | .01 |
| | 25 mg./kg. | 15 | 2.10 | .02 |
| | | 30 | .30 | .3 |
| | 50 mg./kg. | 10 | 2.83 | .001 |
| | | 10 | 2.73 | .001 |
| | | 10 | 2.88 | .01 |
| | | 15 | 4.25 | .001 |
| | | 15 | 4.92 | .001 |
| | | 15 | 5.08 | .001 |
| | | 30 | 1.50 | .01 |
| | | 30 | 3.83 | .01 |
| | | 30 | 3.17 | .01 |
| | | 45 | 2.25 | .01 |
| | | 45 | 5.63 | .01 |
| | | 45 | 2.25 | .01 |
| | | 45 | 1.79 | .01 |
| | | 60 | 2.42 | .001 |
| | | 90 | 1.38 | .01 |
| | | 120 | 1.17 | .05 |

Table 3-continued

| Name of Compound | Oral Dose | Time of Observation (Minutes) | Increase in Reaction Time Over Control | "p" |
|---|---|---|---|---|
| | | 180 | −.13 | .5 |
| | 100 mg./kg. | 5 | .55 | .2 |
| | | 10 | 2.45 | .01 |
| | | 15 | 4.85 | .01 |
| | | 15 | 7.46 | .001 |
| | | 15 | 5.45* | .001 |
| | | 15 | 4.50 | .001 |
| | | 30 | 3.45 | .001 |
| | | 30 | 4.05 | .01 |
| | | 30 | 6.79 | .001 |
| | | 30 | 4.38 | .001 |
| | | 45 | 1.45 | .05 |
| | | 45 | 2.38 | .001 |
| | | 45 | 7.75 | .001 |
| | | 60 | 2.05 | .01 |
| | 200 mg./kg. | 15 | 7.25* | .001 |
| | | 15 | 7.13* | .001 |
| | | 30 | 2.75 | .01 |
| | | 30 | 1.42 | .01 |
| | | 45 | 5.79 | .01 |
| | 300 mg./kg. | 15 | 7.75 | .001 |
| Trans-d(+)-1-cyclopropylmethyl-3a-(m-hydroxyphenyl)-1,2,3,3a,4,5,6,7,7a,8-decahydroisoquinoline maleate | 100 mg./kg. | 30 | 0 | .3 |
| | | 60 | 0 | |
| | | 120 | .40 | .3 |
| | 150 mg./kg. | 15 | 0 | |
| | | 30 | 0 | |
| | | 60 | .35 | .1 |
| | | 120 | .30 | .5 |
| | | 180 | .30 | .5 |
| | 200 mg./kg. | | lethal | |
| Trans-l(−)-1-cyclopropylmethyl-3a-(m-hydroxyphenyl)-1,2,3,3a,4,5,6,7,7a,8-decahydroisoquinoline maleate | 5 mg./kg. | 60 | .20 | .4 |
| | 10 mg./kg. | 60 | .65 | .01 |
| | 25 mg./kg. | 60 | 1.30 | .001 |
| | 50 mg./kg. | 30 | 2.25 | .01 |
| | | 60 | 2.80 | .001 |
| | | 120 | .80 | .05 |
| | 100 mg./kg. | 60 | 3.15 | .001 |
| | 200 mg./kg. | 30 | 4.90* | .001 |
| | | 60 | 5.40 | .001 |
| | | 120 | 2.65 | .001 |

*20 sec. cut off

The above effects could in each instance be blocked by the administration of naloxone.

The ability of the compounds of this invention to antagonize the action of morphine, an opiate, is shown by the following modification of the aforementioned rat tail jerk assay: The standard assay procedure is used with the exception that a 7 amps. current is used instead of a 6 amps. current in the hot wire to decrease the measurable agonist effects of the antagonist. The drugs under test are then administered to groups of rats at different dose levels at different times prior to test, with a 5 mg./kg. dose of morphine invariably being administered 10 minutes prior to test. Positive evidence of antagonism is a decreased reaction time over that to be expected from the morphine. Suggestive evidence of antagonism is the finding of a reaction time less than that to be expected from the morphine dose added to the effect of the analgesic under test as set forth in Tables 2 and 3. Among the compounds of this invention, those in which R in Structure I is cyclopropylmethyl are the preferred antagonists, showing activity in the above test procedure. For example, trans-dl-1-cyclopropylmethyl-3a-(m-hydroxyphenyl)-1,2,3,3a,4,5,6,7,7a,8-decahydroisoquinoline free base at a 50 mg./kg. oral dose administered 30 minutes prior to test reduces the analgesic response to 5 mg./kg. of morphine administered 10 minutes prior to test. The corresponding maleate salt also antagonizes the effects of morphine in the above test. In a series of determinations, it was ascertained that the minimum subcutaneous dose necessary to reduce the analgesic effects of a 5 mg./kg. subcutaneous dose of morphine was in the range 2.5–5.0 mg./kg. and the minimum oral dose, 5–10 mg./kg. Subcutaneous dosages of 50 mg./kg. of the aforementioned maleate salt administered 30 and 60 minutes prior to the assay very effectively blocked the analgesic effect of 5 mg./kg. of morphine.

The optical isomers of the above compound are also opiate antagonist. For example, trans-d(+)-1-cyclopropylmethyl-3a-(m-hydroxypropyl)-1,2,3,3a,4,5,6,7,7a,8-decahydroisoquinoline maleate shows morphine antagonistic effects in the above modified rat tail jerk assay at 100 mg./kg. administered subcutaneously 60 minutes before test. The l(−) isomer shows antagonism at 1–2 mg./kg. administered subcutaneously, and also manifests antagonistic effects in blocking the morphine induced Straub tail in mice. In this assay, a 40 mg./kg. dose of morphine was administered to mice 15 minutes prior to assay, and the test drug at various intervals before assay. Trans-dl-1-cyclopropylmethyl-3a-(m-hydroxyphenyl)-1,2,3,3a,4,5,6,7,7a,8-decahydroisoquinoline maleate gave a 100 percent block of the Straubed tail effected by a subcutaneous injection of 40 mg./kg. of morphine when the test drug was given at a dose of 50 mg./kg. subcutaneously 15 minutes prior to assay, and 80 percent when given 30 minutes prior to assay. The l(−) isomer gave 100 percent blocking on the morphine-induced Straub tail at 50 and 20 mg./kg. doses 15 and 30 minutes before assay.

Trans-dl-1-cyclopropylmethyl-3a-(m-methoxyphenyl)-1,2,3,3a,4.5,6,7,7a,8-decahydroisoquinoline also was found to antagonize morphine in the rat tail jerk assay.

The compounds of this invention have subcutaneous toxicity (L.D.$_{50}$) of about 180–220 mg./kg. in mice and oral toxicity (L.D.$_{50}$) from about 290–400 mg./kg. in mice. The l(—) isomer of trans-dl-1-cyclopropylmethyl-3a-(m-hydroxyphenyl)-1,2,3,3a,4,5,6,7,7a,8-decahydroisoquinoline is less toxic than the dl mixture and the d(+) isomer has about the same toxicity as the dl mixture.

The compounds of this invention can be employed to produce analgesia in mammals by administration by either the parenteral or oral route at a 10–100 mg. dose level. For oral dosage, a suitable quantity of a pharmceutically-acceptable salt of a base according to formula I, formed with a non-toxic acid, is mixed with starch or other excipient, and the mixture placed in telescoping gelatin capsules each containing an analgesic dose. Similarly, the salt can be mixed with starch, a binder, and a lubricant, and the mixture compressed into tablets each containing a standard analgesic dose. The tablets may be scored if lower or divided dosages are to be used. With parenteral administration, the intramuscular or sub-cutaneous routes are preferred. For this purpose, aqueous solutions or suspensions are employed using a pharmaceutically-acceptable salt of the amine base of formula 1. In general, modes of administration and pharmaceutical forms found useful in the past for morphine, codeine, methadon, meperidine and other opiate-like analgesics can be adopted by those skilled in the art for the compounds of this invention. The dosages for the dl racemates and the l isomers are in the range 10–100 mg. and preferably in the range 25–50 mg.

We claim:

1. A compound of the formula:

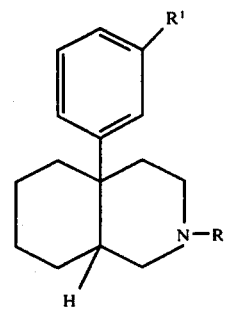

wherein
R is cyclopropylmethyl or cyclobutylmethyl;
R' is O-alk, OH, or

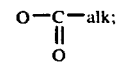

and
alk is ($C_1$–$C_3$) alkyl and pharmaceutically-acceptable acid-addition salts thereof 2. A compound according to claim 1 in which R' is OH.

3. A compound according to claim 1 in which R' is O-alk and alk is ($C_1$–$C_3$) alkyl.

4. A compound according to claim 1 in which R is cyclopropylmethyl.

5. A compound according to claim 1, said compound being trans-dl-1-cyclobutylmethyl-3a-(m-hydroxyphenyl)-1,2,3,3a,4,5,6,7,7a,8-decahydroisoquinoline.

6. A compound according to claim 1, said compound being trans-dl-1-cyclopropylmethyl-3a-(m-hydroxyphenyl)-1,2,3,3a,4,5,6,7,7a,8-decahydroisoquinoline.

7. A compound according to claim 1, said compound being trans-l(—)-1-cyclopropylmethyl-3a-(m-hydroxyphenyl)-1,2,3,3a,4,5,6,7,7a,8-decahydroisoquinoline.

8. A trans-dl racemate of a compound according to claim 1.

9. A trans-dl of a compound according to claim 1 in which R' is OH.

* * * * *

UNITED STATES PATENT OFFICE
CERTIFICATE OF CORRECTION

PATENT NO. : 4,001,248
DATED : January 4, 1977
INVENTOR(S) : Dennis M. Zimmerman, et al.

It is certified that error appears in the above-identified patent and that said Letters Patent are hereby corrected as shown below:

Column 1, line 15, "replace" should be --replaced--.

Column 4, line 3, "are" should be --the--.

Column 6, line 7, "trans-dl l race-" should be --trans-dl race- --

Column 8, line 35, "255 g." should be --225 g.-- .

Column 9, line 58, "extraced" should be --extracted--.

Column 11, line 22, "aqueous a-(m-Hydroxyphenyl acid." should read --aqueous acetic acid.--

Column 11, line 32, "3-(m-Hydrox-" should read --3a-(m-Hydrox-

Column 11, line 47, "and was the" should read --and was then

Column 13, line 23, "197.°" should read --197.5°--

UNITED STATES PATENT OFFICE
CERTIFICATE OF CORRECTION

Patent No. 4,001,248  Dated January 4, 1977

Inventor(s) Dennis M. Zimmerman et al.

It is certified that error appears in the above-identified patent and that said Letters Patent are hereby corrected as shown below:

Column 22, line 43, after "trans-dl" insert -- racemate --.

Signed and Sealed this

Thirty-first Day of May 1977

[SEAL]

Attest:

RUTH C. MASON
Attesting Officer

C. MARSHALL DANN
Commissioner of Patents and Trademarks

Notice of Adverse Decision in Interference

In Interference No. 100,293, involving Patent No. 4,001,248, D. M. Zimmerman and W. S. Marshall, N-CYCLOALKYLMETHYL DECAHYDROISOQUINOLINES, final judgment adverse to the patentees was rendered May 26, 1982, as to claim 1.

[*Official Gazette October 19, 1982.*]